United States Patent [19]

Braca et al.

[11] 4,189,441

[45] Feb. 19, 1980

[54] PROCESS FOR PREPARING ESTERS FROM ETHERS OR ESTERS OF LOWER HOMOLOGOUS ALCOHOLS

[75] Inventors: Giuseppe Braca; Glauco Sbrana, both of Pisa; Guglielmo Gregorio, Milan, all of Italy

[73] Assignee: Montedison S.p.A., Milan, Italy

[21] Appl. No.: 818,857

[22] Filed: Jul. 25, 1977

[30] Foreign Application Priority Data

Jul. 28, 1976 [IT] Italy ................................ 25782 A/76
Apr. 7, 1977 [IT] Italy ................................ 22223 A/77

[51] Int. Cl.² .................... C07C 67/28; C07C 67/37
[52] U.S. Cl. ............................ 260/410.9 R; 260/343; 260/343.5; 260/343.6; 260/413; 560/232; 560/265; 562/517; 568/671; 568/885; 568/907
[58] Field of Search ............... 260/491, 496, 468 K, 260/476 R, 410.9 R; 560/232, 265, 240

[56] References Cited

U.S. PATENT DOCUMENTS 3,855,307 12/1974 Rony et al. ..................... 260/488 K Primary Examiner—Vivian Garner
Attorney, Agent, or Firm—Stevens, Davis, Miller & Mosher

[57] ABSTRACT

A process is disclosed for preparing esters having the general formulae:

RCOOCH$_2$R' and

R'COOCH$_2$R wherein R and R' are linear or branched alkyl radicals either like or unlike each other, and containing from 1 to 16 carbon atoms, or considered together, forming a cycloaliphatic ring having up to 7 carbon atoms, wherein carbon monoxide and hydrogen are reacted, at temperatures ranging from 150° to 350° C. and at pressures ranging from 50 to 1000 atmospheres, with an ether of formula R O R' or esters of formula RCOOR' and R'COOR, in which R and R' have the same meanings as specified hereinabove, and in the presence of a catalyst system comprising a ruthenium carbonyl and a promoter selected from the class consisting of hydroiodic acid, carboxylic acid solutions of inorganic or tetraalkylammonium bromides and iodides, and mixtures of these promoters.

8 Claims, No Drawings

PROCESS FOR PREPARING ESTERS FROM ETHERS OR ESTERS OF LOWER HOMOLOGOUS ALCOHOLS

The present invention relates to a process for preparing esters. More particularly, it relates to the preparation of higher esters by carbonylation of ethers or esters of lower homologous alcohols. Such compounds are useful, e.g., as solvents in numerous application fields.

It is already known how to prepare esters of aliphatic carboxylic acids, starting from alcohols having one carbon atom less than the acid or from the ethers derived from said alcohols, by reaction thereof with carbon monoxide and hydrogen at high temperatures and pressures, with catalysts consisting of cobalt or nickel (U.S. Pat. No. 2,457,204; Y. Y. Aliev et al., Dokl. Akad. Nauk Uzbek SSR, 1960 (9) 37).

It is known too that such esters are by-products of the synthesis of carboxylic acids from alcohols: for example, methyl acetate is a by-product of the synthesis of acetic acid from methanol catalyzed by cobalt (German Pat. No. 921,938) or by rhodium (Italian Pat. No. 836,365).

Considering the esters as compounds derived from the reaction between an acid and an alcohol by elimination of a water molecule, the processes reported hereinbefore permit one always to obtain esters of the starting alcohol or in case one starts from an ether, esters of the alcohol, of which the ether may be considered as a derivative. Only the acid radical has in its chain a carbon atom more than the starting compounds.

It is furthermore known how to add carbon monoxide and hydrogen to an alcohol in order to obtain the higher homologous alcohol: such processes, however, take place under different conditions and do not bring about any corresponding esters (U.S. Pat. No. 3,285,948).

It has now been found that by carbonylation of ethers or esters it is possible to attain good yields of esters of higher homologous alcohols in respect to those which the starting products may be considered as derived from, provided the reaction is conducted in the presence of a catalyst system composed or consisting essentially of ruthenium carbonyls and a promoter selected from the class consisting of iodine or bromine compounds in the presence of a solvent.

Thus, a principal object of the present invention is to provide a process for preparing esters having the general formulae:

$$RCOOCH_2R'$$

and $$R'COOCH_2R$$

in which R and R' are linear or branched alkyl radicals either like or unlike each other, and containing from 1 to 16 carbon atoms, or considered together, they may form a cycloaliphatic ring having up to 7 carbon atoms, the process being characterized in that carbon monoxide and hydrogen are reacted, at temperatures between 150° and 350° C. and at pressures between 50 and 1000 atmospheres, e.g., from 100 to 400 atmospheres, with an ether of formula: ROR' or esters of formula: RCOOR' or R'COOR, in which R and R' have the same meanings as specified hereinabove, in the presence of a catalytic system composed or consisting essentially of ruthenium carbonyls and a promoter selected from the class consisting of hydroiodic acid, a carboxylic acid solution of inorganic or tetraalkyl ammonium bromides or iodides, and a mixture of such promoters.

The process according to this invention may be represented by one of the following reactions:

$$ROR' + CO + H_2 \rightarrow RCOOCH_2R' + R'COOCH_2R \quad (1)$$

$$RCOOR' + CO + H_2 \rightarrow RCOOCH_2R' \quad (2)$$

$$R'COOR + CO + H_2 \rightarrow R'COOCH_2R \quad (3)$$

When practicing the process starting from the ethers according to reaction (1), it is assumed that, as an intermediate reaction, the esters constituting the starting products of reactions (2) and (3) may form.

This intermediate reaction (which, however, has already been indicated as possible under different conditions and with other catalyst systems) may be represented as follows:

$$R'OR + CO \rightarrow RCOOR' + R'COOR \quad (4)$$

Thus, for example, by reacting carbon monoxide and hydrogen with dimethylether a mixture of products is obtained, that prevailingly consists of methyl acetate and ethyl acetate in ratios varying according to the reaction conditions.

Since a reaction collateral to the reaction which gives rise to the formation of the desired products, that is of the homologous higher esters R COOCH$_2$R' and R'COOCH$_2$R, starting from ROR' ether, may be represented as an attack by the carboxylic acid, used as a solvent, on the starting ether, there prove to be suitable for use as solvents in the process according to this invention the carboxylic acids of formula R"COOH whose R" radical is equal to or different from R and R' (as defined above) and represents an alkyl or cycloalkyl radical having up to 8 carbon atoms.

Preferred are the carboxylic acids whose radical R" is equal to R or R' since in such case the esters that form are intermediates in the synthesis of the end products. Those acids may, moreover, be present in their turn as by-products of the reaction according to the process under consideration.

Thus, for instance, in the carbonylation reaction of dimethylether to ethyl acetate, a particularly desirable solvent is acetic acid. Operating with such a solvent, in fact, brings about the formation of methyl acetate which may be considered as an intermediate product in the main synthesis, and thus without accumulating in the reaction mixtures.

Moreover, the acetic acid forms as a by-product of the carbonylation reaction, and under suitable conditions, the quantity produced corresponds to the amount consumed.

Ruthenium compounds suited for use in the process according to this invention are either ruthenium carbonyls such as Ru$_3$(CO)$_{12}$; Ru(CO)$_4$I$_2$; RuCl (p-C$_3$H$_5$)(CO)$_3$; [Ru(CO)$_3$Br$_2$]$_2$; or compounds that, under the reaction conditions, give rise to the formation of ruthenium carbonyls "in situ", such as, for example, subdivided metallic ruthenium; ruthenium acetylacetonate; ruthenium salts of carboxylic acids; sodium hexachloro-ruthenate; ammonium hexachloro-ruthenate; ruthenium triiodide; ruthenium tribromide; etc.

Compounds suitable for use as promoter in the above mentioned catalytic system are hydroiodic acid or its precursors such as elementary iodine or its organic compounds (which, as is known from M. Busch & H. Stove in Berichte, Vol. 49, 1063 (1916), in the presence of hydrogen at high temperatures yield HI), and a carboxylic acid solution of inorganic iodides or bromides, or iodides or bromides of tetraalkylammonium. Carboxylic acid solutions of: iodides of Na, K, Fe, Co, Ni, Zn, Cd and $Sn^{++}$; bromides of Na and K; tetraalkylammonium iodides and bromides and mixtures thereof are suitable for use as promoters.

Preferred organic iodides are the alkyl or alkylaryl iodides having from 1 to 20 carbon atoms.

Preferred carboxylic acid solutions are acetic and propionic acid solutions of the alkali metal iodides and bromides, of the alkaline-earth metal iodides and bromides, of the Fe, Co, Ni, Zn, Cd, $Sn^{++}$ iodides, of the tetraalkylammonium iodides, or mixtures thereof.

The iodine/ruthenium atomic ratios that are particularly suited for use in the process according to this invention are between 2 and 10.

The reaction is conducted at a temperature ranging from 150° to 350° C., and preferably from 180° to 250° C.

The $H_2+CO$ partial pressure should be at least 50 atmospheres, and preferably between 100 and 300 atmospheres, the total pressure being such as to insure that at least a part of the reagents shall be in the liquid phase.

The $H_2/CO$ molar ratio in the reacting mixture may range from 0.1 to 2. Higher hydrogen concentrations do not adversely affect the reaction trend, but may limit its selectivity, thus favoring the formation of methane.

The reaction medium best suited for carrying out the process consists in the reagents themselves or in the reaction by-products, in which the catalyst is dissolved.

It is possible to use solvents such as aromatic hydrocarbons, for example toluene, or a carboxylic acid as above defined, even when the latter is not expressly required by the catalytic systems referred to above, or their esters and mixtures of said acids and their esters.

A reacting mixture particularly suitable for carrying out the process according to this invention is made up of an ether with the ester, or a mixture of esters, RCOOR'+R'COOR, that are generally less volatile than the ether itself.

According to the present invention, the catalytic system as defined herein, the solvent, and the ether or the ester, or mixtures thereof, are fed to an autoclave in a $H_2$ and CO atmosphere. The autoclave is heated to the desired reaction temperature, the desired pressure being maintained by feeding in a $H_2+CO$ mixture in such amounts as are necessary for that purpose.

At the conclusion of the reaction, the useful reaction products may be easily separated by conventional fractional distillation of the obtained mixtures. The by-products (non-homologous esters and non-esterified carboxylic acids) may be employed again in the reaction.

The process according to this invention offers several important advantages: the main advantage consists in the possibility of utilizing, for the preparation of the higher homologous esters, the by-products of other processing procedures, e.g., dimethylether which is a by-product of the well known methanol synthesis, and methyl acetate which is a by-product of the well known acetic acid synthesis. Another marked advantage of the process consists in being able to carry out the reaction in one step.

The following detailed working examples are given in order still better to illustrate the invention:

EXAMPLE 1

25 ml of toluene, 0.38 m.moles of RuCl ($\eta$-$C_3H_5$)(CO)$_3$ (prepared according to the method described by G. Sbrana, G. Braca, F. Piacenti and P. Pino, J. Organometal. Chem., 13, 240 (1968)) and 1.52 m.moles of $CH_3I$, corresponding to an I/Ru ratio=4, were charged into a 100 $cm^3$ autoclave made of Hastelloy C.

0.195 m.moles of gaseous dimethylether were condensed in the autoclave cooled down under vacuum, whereupon 50 atm. of $H_2$ and 100 atm. of CO were fed into the autoclave. The autoclave was then heated to 200° C. while maintaining a pressure of 240 atmospheres by feeding the $H_2+CO$ mixture in a 2:1 molar ratio.

After 18.5 hours the autoclave was cooled down, the resulting solution being markedly acid, and the products were subjected to a gas chromatographic analysis.

The conversion of the starting ether was 42.5%, the yields—referred to the converted product—of the products listed hereinbelow being as follows:

$CH_4$=12.8%

Alcohols (Me, Et, Pr)=13.0%

Higher ethers=4.5%

Methyl acetate=42.3%

Ethyl acetate=16.0%

Acids (acetic, propionic)=6.0%

EXAMPLES 2-8

A number of carbonylation tests conducted at a temperature of about 200° C. is reported on the following table where the catalyst concentration was $1.5 \cdot 10^{-2}$ gram atoms/liter.

| Examples | CATALYST SYSTEM TYPE | REACTION CONDITIONS | | | | | | | REACTION PRODUCTS | | |
|---|---|---|---|---|---|---|---|---|---|---|---|
| | | I/Ru Ratio | REAGENT and SOLVENT (moles) | initial CO press., atm | initial $H_2$ press., atm | $H_2/CO$ initial (final) | P/ in hot conditions, atm | Time required, hours | $H_2/CO$ fed | Conv. % | YIELDS* Product (moles) | % |
| 2 | $Ru(CO)_4I_2$ /$CH_3I$ | 10 | dimethylether (0.125) toluene (25 ml) | 100 | 50 | 0.5 (1.1) | 242–265 | 28.5 | 2 | 84.8 $CO_2$ % 8.4 | $CH_4$ Alcohols (Me, Et, Pr) Higher ethers Methyl acetate Ethyl abetate Other esters Acids | 21.6 2.3 3.2 20.7 19.3 4.3 18.8 |
| 3 | $Ru(Acac)_3$ /$CH_3I$ | 10 | dimethylether (0.125) toluene (25 ml) | 100 | 50 | 0.5 (0.77) | 235–280 | 28.5 | 1 | 86 | $CH_4$ Alcohols (Me, Et, Pr) Higher ethers | 20.8 2.9 3.5 |

-continued

| Examples | CATALYST SYSTEM TYPE | I/Ru Ratio | REAGENT and SOLVENT (moles) | initial CO press., atm | initial H2 press., atm | H2/CO initial (final) | P/ in hot conditions, atm | Time required, hours | H2/CO fed | Conv. % | Product (moles) | % |
|---|---|---|---|---|---|---|---|---|---|---|---|---|
| | | | | | | | | | | CO2 % 3.0 | Methyl acetate | 31.7 |
| | | | | | | | | | | | Ethyl acetate | 18.4 |
| | | | | | | | | | | | Methyl propionate | 3.6 |
| | | | | | | | | | | | Acids** | 17.8 |
| 4 | Ru(Acac)3 /CH3I | 10 | dimethylether (0.124) toluene (25 ml) | 125 | 25 | 0.2 (0.92) | 240–270 | 28.5 | 1 | | CH4 | 7.9 |
| | | | | | | | | | | | Alcohols (Me, Et, Pr) | 1.3 |
| | | | | | | | | | | 92 | Higher ethers | 3.8 |
| | | | | | | | | | | | Methyl acetate | 50.1 |
| | | | | | | | | | | CO2 % 1.1 | Ethyl acetate | 18.4 |
| | | | | | | | | | | | Methyl propionate | 3.3 |
| | | | | | | | | | | | Acids** | 15.0 |
| 5 | Ru(Acac)3 /CH3I | 10 | dimethylether (0.1) acetic acid (0.430) | 135 | 30 | 0.22 (0.49) | 250–270 | 26.5 | 0.5 | >95$^a$ 21$^b$ | CH4 | 10.8 |
| | | | | | | | | | | | Alcohols (Me, Et) | 2.6 |
| | | | | | | | | | | CO2 % 2.0 | Higher ethers | 2.4 |
| | | | | | | | | | | | Methyl acetate | 42.3 |
| | | | | | | | | | | | Ethyl acetate Acetic acid (0.343) | 42.2 |
| | | | | | | | | | | | Propionic acid (0.008) | |
| 6 | RuCl(7—C3H5)(CO)3/CH3I | 4 | diethylether (0.20) toluene (25 ml) | 100 | 50 | 0.5 (0.60) | 238–262 | 15 | 2 | 54.3 | C2H6 | 21.8 |
| | | | | | | | | | | | Alcohols | 8.7 |
| | | | | | | | | | | | Higher ethers | 3.6 |
| | | | | | | | | | | | Ethyl propionate | 46.7 |
| | | | | | | | | | | | Propyl propionate | 2.7 |
| | | | | | | | | | | | Acids | 5.3 |
| 7 | RuCl(η—C3H5)(CO)3/CH3I | 8 | methyl acetate (0.364) | 88 | 67 | 0.76 (1.0) | 240–260 | 16 | 2 | 33.2 | CH4 | 12.9 |
| | | | | | | | | | | | Alcohols | 9.4 |
| | | | | | | | | | | | Acids | 29.4 |
| | | | | | | | | | | | Ethyl acetate | 46.7 |
| | | | | | | | | | | | Propylacetate | 2.4 |
| | | | | | | | | | | CO2 % <1 | | |
| 8 | Ru(Acac)3 /CH3I | 10 | dimethylether (0.123) methyl acetate (0.312) | 125 | 25 | 0.2 (0.62) | 235–270 | 28 | 0.5 | 99.8$^a$ 30.4$^c$ | CH4 | 10.8 |
| | | | | | | | | | | | Alcohol | 2.9 |
| | | | | | | | | | | CO2 % 1.0 | Ethers + acetal | 1.5 |
| | | | | | | | | | | | Acids | 32.2 |
| | | | | | | | | | | | Ethyl acetate | 44.6 |

*calculated in respect to the disappeared reagent
**calculated on the reacted dimethylether
$^a$dimethylether conversion
$^b$acetic acid conversion
$^c$methyl acetate conversion

EXAMPLE 9

The following test was carried out to prove that if no free HI is present in the reacting medium, the reaction does not take place.

By operating as described in Example 1, 0.15 moles of methyl acetate, 0.38 m.moles of Ru(CO)4I2 (the I/Ru ratio being=2), and 0.061 moles of dimethylether were charged into a 100 cm³ autoclave.

Successively, 25 atm. of H2 and 125 atm. of CO in a H2/CO ratio=0.2 were fed into the autoclave. The autoclave was then heated to 200° C., while maintaining a pressure of 260 atmospheres. After 8 hours the reaction had practically not proceeded: only negligible amounts of alcohols, methane and acetic acid were obtained. The discharged solution was practically neutral.

EXAMPLE 10

Into a Hastelloy C autoclave having a holding capacity of 100 cm³, were introduced 0.1 moles of dimethylether, and 0.43 moles of acetic acid. The catalytic system, consisting of ruthenium trisacetylacetonate (0.4 m.moles) and sodium iodide (4 m.moles), corresponding to an I/Ru ratio=10, was fed in with the solvent.

The autoclave was then pressurized with a H2+CO mixture in a molar ratio H2:CO=0.5 at 150 atm., and the temperature was brought up to 200° C., maintaining for 28 hours a pressure of 250 atm. Once the reaction was completed, the products were discharged and then analyzed by means of gas chromatography.

There was thus obtained a conversion of the starting ether amounting to 70%, and with the following selectivities:

Methane=4.4%
Methyl alcohol=2.1%
Propyl alcohol=0.3%
Propionic acid=0.6%
Ethyl ether=1.1%
Methyl acetate=12%
Ethyl acetate=79%

EXAMPLE 11

To a solution containing the catalytic system used in Example 10, and recovered by the distillation of the reaction products and of part of the acetic acid, there were added dimethylether and acetic acid in such amounts as to arrive respectively at 0.1 moles and 0.43 moles for these two components.

Operating under the same conditions as those described above in Example 10 for 8 hours, there was obtained a conversion of 70% and the following selectivities:

Methane=traces
Methyl alcohol=0.6%
Ethyl ether=0.2%
Methylethylether=0.4%
Methyl acetate=38.7%
Ethyl acetate=54.6%

EXAMPLE 12

Operating as indicated above in Example 10, into a Hastelloy C autoclave of 100 cc holding capacity there were introduced 0.1 moles of dimethylether and 0.43 moles of propionic acid. The catalytic system, consisting of $Ru(CO)_4I_2$ (0.4 m.moles) and NaI (4 m.moles) equal to an I/Ru ratio of 10, was fed in with the solvent.

Thereupon the autoclave was pressurized with an $H_2+CO$ mixture having a molar ratio $H_2:CO=1$ at 150 atm., while the temperature was brought up to 200° C., the pressure being then maintained for 18 hours at 250 atm.

Once the reaction was completed, the products were discharged and then analyzed by gas chromatography.

In this way there was obtained a 70% conversion and the following selectivities:

Methane=4%
Ethyl alcohol=0.36%
Propionic acid=3%
Methylethyl ether=0.284%
Methyl acetate=2.5%
Ethyl acetate=56.8%
Methyl propionate=15.15%
Ethyl propionate=11%
Propyl propionate=9.6%

EXAMPLE 13

A mixture consisting of 0.1 moles of dimethylether, 0.23 moles of acetic acid, and 0.19 moles of methyl acetate was made to react for 25 hours under the same conditions as those described above in Example 10 and with the same catalytic system.

There was thus obtained a conversion of the starting ether amounting to 54.3% and the following selectivities:

Methane=9.2%
Ethyl alcohol=0.5%
Acetic acid=10.5%
Ethyl acetate=60.6%
Propyl acetate=1%

EXAMPLE 14

A mixture of 0.1 moles of dimethylether and 0.43 moles of acetic acid was made to react, operating under the same conditions as those described above in Example 10 in the presence of a catalytic system consisting of 0.4 m.moles of ruthenium trisacetylacetonate and 4 m.moles of NaBr, for a period of 28 hours.

There was observed a conversion of the dimethylether amounting to 54.8% and the following selectivities:

Methylethyl ether=0.2%
Ethyl ether=0.9%
Methyl acetate=34.3%
Ethyl acetate=8.9%

EXAMPLE 15

Operating as indicated above in Example 10, into a Hastelloy C autoclave of 100 cc holding capacity there were introduced 0.1 moles of dimethylether and 0.43 moles of acetic acid. The catalytic system consisting of 0.4 m.moles of ruthenium trisacetylacetonate and 4 m.moles of $CH_3I$ equal to an I/Ru ratio=10 was fed in with the solvent.

The autoclave was then pressurized with a $H_2+CO$ mixture in a molar ratio $H_2:CO=0.5$ at 150 atm. and the temperature was brought up to 200° C., while maintaining for 28 hours a pressure of 250 atm.

There was thus obtained a conversion of the starting ether amounting to 95% with the following selectivities:

Methane=5%
Methyl alcohol=1.2%
Propyl alcohol=2.3%
Ethyl ether=1.0%
Methyl acetate=38.4%
Ethyl acetate=38.0%

EXAMPLE 16

A mixture consisting of 0.1 moles of dimethylether, 0.25 moles of acetic acid, and 0.19 moles of methyl acetate was introduced into the autoclave by using the same catalytic system as described above in Example 15.

The autoclave was then pressurized with a $H_2+CO$ mixture in a molar ratio $H_2:CO=1$ at 150 atm., and the temperature was brought up to 200° C., while maintaining for 14 hours a pressure of 250 atm.

There was thus obtained a conversion of the starting ether amounting to 58.4% with the following selectivities:

Methane=8.6%
Methyl alcohol=5.5%
Ethyl alcohol=1.55%
Acetic acid=1%
Propionic acid=1.2%
Methylethylether=2.3%
Ethyl ether=0.7%
Ethyl acetate=73%
Methyl propionate=0.5%
Ethyl propionate=0.13%

EXAMPLE 17

A mixture consisting of 0.1 moles of dimethylether, 0.23 moles of acetic acid, and 0.19 moles of methylacetate was made to react for 15.5 hours under the same conditions as described above in Example 16. The catalytic system consisted of 0.4 m.moles of ruthenium trisacetylacetonate and 2 m.moles of $CH_3I$ and 1 m.mole of $NiI_2.6H_2O$ corresponding to an I/Ru ratio=10.

A conversion of 76.2% was obtained with the following selectivities:

Methane=9.66%
Methyl alcohol=4.65%
Ethyl alcohol=1.95%
Acetic acid=0.95%
Methyl formate=0.22%
Methylethylether=0.75%
Ethyl ether=traces
Ethyl acetate=79.2%
Methyl propionate=2.26%

EXAMPLE 18

A mixture consisting of 0.2 moles of dimethylether, 0.15 moles of acetic acid, and 0.13 moles of methylacetate was made to react for 5 hours at 200° C. and a pressure of 350 atm. The catalytic system consisted of 0.66 m.moles of ruthenium tris-acetylacetonate, 2 m.moles of $CH_3I$ and 4 m.moles of NaI corresponding to an I/Ru ratio =10.

A conversion of 35% of dimethylether was obtained with the following selectivities:

Methane=5%
Methyl alcohol=10.2%
Ethyl alcohol=2.1%
Methyl formate=1.3%
Methylethylether=2.7%
Ethyl ether=10.1%
Ethyl acetate=68%

What is claimed is:

1. A process for preparing esters having the general formulae:

$$RCOOCH_2R'$$

and $$R'COOCH_2R$$

wherein R and R' are linear or branched alkyl radicals either like or unlike each other, and containing from 1 to 16 carbon atoms, wherein carbon monoxide and hydrogen are reacted, at temperatures ranging from 150° to 350° C. and at pressures ranging from 50 to 1000 atmospheres, with a compound selected from the class consisting of an ester of formula RCOOR', an ester of formula R'COOR and an ether of formula ROR', or with a mixture thereof, in which R and R' have the same meanings as specified hereinabove, and in the presence of a catalyst system consisting essentially of a ruthenium carbonyl and a promoter selected from the class consisting of hydroiodic acid, carboxylic acid solutions of inorganic or tetraalkylammonium bromides and iodides, and mixtures of these promoters.

2. A process as defined in claim 1, in which $Ru_3(CO)_{12}$, $[Ru(CO)_3Br_2]_2$, $Ru(CO)_4I_2$, or $RuCl\ (\eta\text{-}C_3H_5)(CO)_3$ is employed as the ruthenium carbonyl of the catalyst system.

3. A process as defined in claim 1, in which the ruthenium carbonyl is formed "in situ" from subdivided metallic ruthenium, ruthenium acetylacetonate, a ruthenium salt of a carboxylic acid, sodium hexachlororuthenate, ruthenium triiodide, ammoniumhexachlororuthenate, or ruthenium tribromide.

4. A process as defined in claim 1, in which the promoter is selected from the class consisting of carboxylic acid solutions of inorganic iodide and bromide salts and tetraalkylammonium iodides and bromides.

5. A process as defined in claim 1, in which the promoter is selected from the class consisting of carboxylic acid solutions of iodides of Na, K, Fe, Co, Ni, Zn, Cd and $Sn^{++}$; bromides of Na and K; tetraalkylammonium iodides and bromides and mixtures thereof; hydroiodic acid and iodine compounds capable of forming HI under the reaction conditions selected from among elementary iodine and alkyl- and alkylaryl-iodides having from 1 to 20 carbon atoms.

6. A process as defined in claim 1, in which the carboxylic acid is acetic acid or propionic acid.

7. A process as defined in claim 1, in which the reaction is conducted at a temperature ranging from 180° to 250° C. and at a pressure ranging from 100 to 400 atmospheres.

8. A process as defined in claim 1, wherein the reaction is conducted in the presence of a solvent selected from the class consisting of carboxylic acids having up to 8 carbon atoms, their esters, and mixtures of said acids and their esters, and aromatic hydrocarbons.

* * * * *